United States Patent
Chazan et al.

(10) Patent No.: US 8,206,311 B2
(45) Date of Patent: Jun. 26, 2012

(54) ANALYZER FOR NITRIC OXIDE IN EXHALED BREATH WITH MULTIPLE-USE SENSOR

(75) Inventors: David J. Chazan, Palo Alto, CA (US); Bhairavi R. Parikh, Palo Alto, CA (US); Bryan P. Flaherty, Half Moon Bay, CA (US); David J. Anvar, Sunnyvale, CA (US); Brian A. Awabdy, Pleasanton, CA (US)

(73) Assignee: Aerocrine AB, Solna (SE)

( * ) Notice: Subject to any disclaimer, the term of this patent is extended or adjusted under 35 U.S.C. 154(b) by 542 days.

(21) Appl. No.: 12/416,760

(22) Filed: Apr. 1, 2009

(65) Prior Publication Data

US 2010/0256514 A1    Oct. 7, 2010

(51) Int. Cl.
*A61B 5/08* (2006.01)
*G01N 33/497* (2006.01)

(52) U.S. Cl. ........ 600/532; 73/23.3; 422/86; 435/287.1; 435/25

(58) Field of Classification Search .................. 600/300, 600/529–545; 250/390.04, 390.07, 362–361 C; 73/23.3, 23.22, 23.35; 422/84–86

See application file for complete search history.

(56) References Cited

U.S. PATENT DOCUMENTS

| | | | |
|---|---|---|---|
| 4,290,296 A * | 9/1981 | Bredeweg et al. | 73/1.07 |
| 5,009,231 A * | 4/1991 | Schmitt et al. | 600/476 |
| 2004/0017570 A1 * | 1/2004 | Parikh et al. | 356/437 |
| 2005/0240115 A1 * | 10/2005 | Fay et al. | 600/532 |
| 2005/0241382 A1 * | 11/2005 | Coenen | 73/152.19 |
| 2006/0177890 A1 * | 8/2006 | Anvar et al. | 435/27 |
| 2007/0086920 A1 * | 4/2007 | Anvar et al. | 422/87 |
| 2008/0110269 A1 * | 5/2008 | Strietzel et al. | 73/718 |
| 2009/0274600 A1 * | 11/2009 | Jain et al. | 423/219 |

OTHER PUBLICATIONS

Aylott et al., "Optical Biosensing of Gaseous Nitric Oxide Using Spin-Coated Sol-Gel Thin Films," 1997, Chem. Mater., 9, 2261-2263.*

* cited by examiner

*Primary Examiner* — Charles A Marmor, II
*Assistant Examiner* — Eric Messersmith
(74) *Attorney, Agent, or Firm* — Renner, Otto, Boisselle & Sklar, LLP

(57) ABSTRACT

A high-sensitivity analyzer for nitric oxide in exhaled breath at levels of 200 ppb or less with a sensor containing cytochrome C is rendered capable of multiple uses without the need for installing a new sensor for each use. This capability is achieved by regenerating the analyzer after each use by purging the sensor and surrounding regions with $NO_x$-free air in a controlled manner, preferably in pulses separated by equilibration periods.

14 Claims, 1 Drawing Sheet

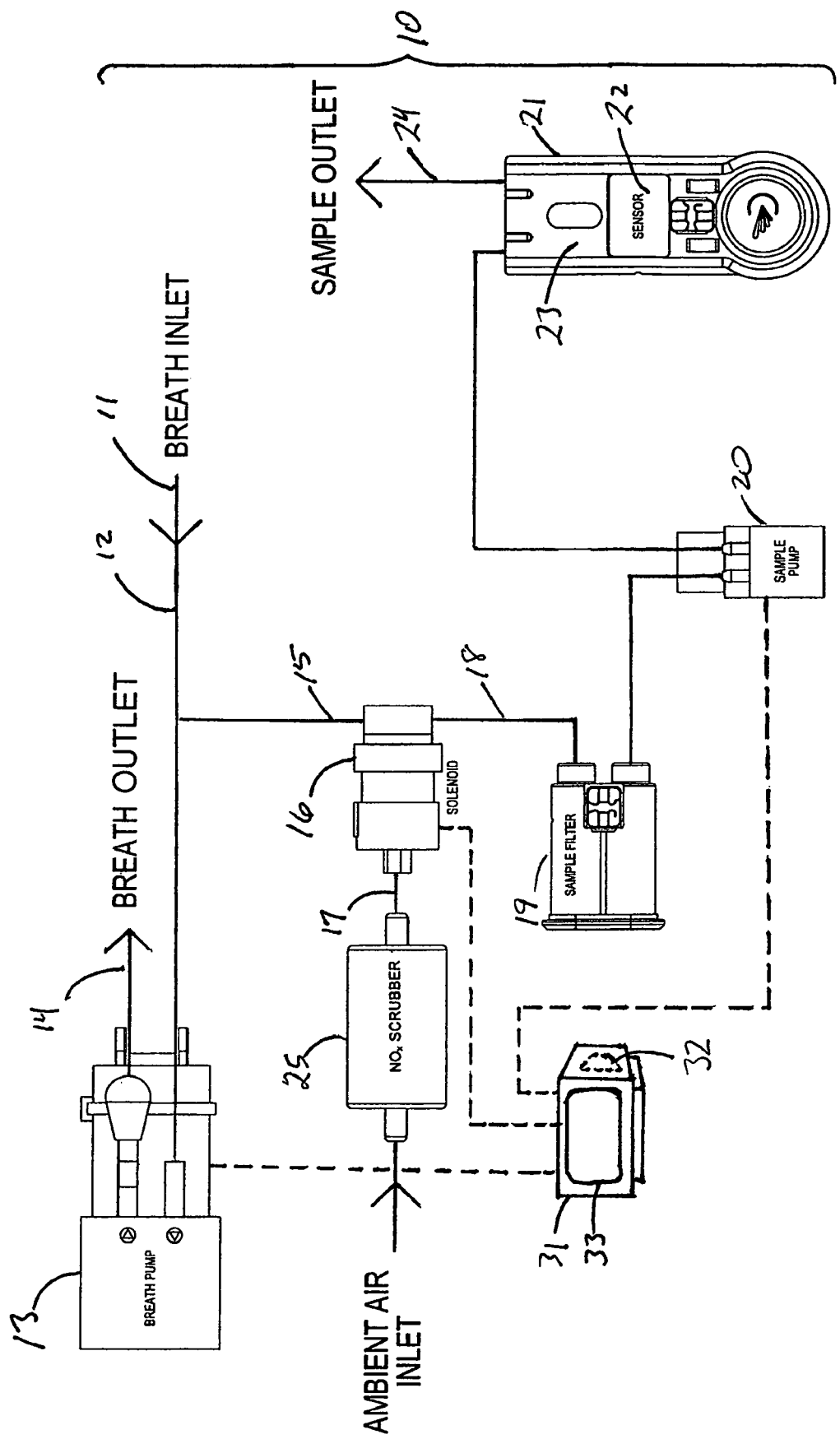

ANALYZER FOR NITRIC OXIDE IN EXHALED BREATH WITH MULTIPLE-USE SENSOR

BACKGROUND OF THE INVENTION

1. Field of the Invention

This invention lies in the field of exhaled breath analyzers for monitoring pulmonary conditions.

2. Description of the Prior Art

Persons suffering from asthma are able to monitor the intensity of their condition and to predict the likelihood of an asthmatic attack by monitoring the level of nitric oxide (NO) in their exhaled breath. Instruments that detect nitric oxide levels in exhaled breath are disclosed in Silkoff, U.S. Pat. No. 5,795,787, issued Aug. 18, 1998; Silkoff et al., U.S. Pat. No. 6,010,459, issued Jan. 4, 2000; Parikh et al., United States Pre-Grant Publication No. US 2004-0017570 A1, published Jan. 29, 2004; Flaherty et al., United States Pre-Grant Publication No. US 2005-0083527 A1, published Apr. 21, 2005, and corresponding U.S. Pat. No. 7,220,387, issued May 22, 2007; Parikh et al., United States Pre-Grant Publication No. US 2005-0053549 A1, published Mar. 10, 2005; Flaherty et al., US 2007-0261472 A1, published Oct. 15, 2007; Nason et al., United States Pre-Grant Publication No. US 2006-0195040 A1, published Aug. 31, 2006; Chazan, United States Pre-Grant Publication No. US 2006-0177890 A1, published Aug. 10, 2006; and Anvar et al., United States Pre-Grant Publication No. US 2007-0086920 A1, published Apr. 19, 2007. The instruments described in these documents contain nitric oxide sensors retained in flow-through passages for direct contact with an individual's exhaled breath, together with pumps, filters, and various detectors and controls that allow the user to detect nitric oxide levels in the breath, and changes in such levels, in the parts-per-billion range.

The sensor is typically a nitric oxide-binding protein such as cytochrome C that undergoes an optically detectable change upon binding to nitric oxide. To achieve high sensitivity and stability, the protein is encapsulated in a support matrix at a controlled concentration, the matrix having a controlled porosity and surface area. Preferred matrices are xerogels and aerogels. Despite these controls, the sensor is subject to variability since the binding equilibria between the protein and the nitric oxide are significantly affected by other components in the system, even those in minute amounts, including extraneous species present in the breath samples, the atmosphere, and the instrument itself. As a result, the typical sensor is conditioned for use by the manufacturer and then used only once, requiring a fresh sensor for each use.

SUMMARY OF THE INVENTION

It has now been discovered that components of a nitric oxide sensor in an exhaled breath monitoring system that affect the sensitivity and reproducibility of the system can be conditioned between breath samples by the system itself to reverse the effects of a breath sample exposure and return the sensor to its original state, thereby allowing the sensor to be re-used. This invention thus resides in an analyzer whose sensor can be used two or more times and up to thirty times or more before replacement with a new, unused sensor. The invention also resides in a method for regenerating a nitric oxide analyzer between breath samples, preferably with automated operating components within the analyzer itself. This capability is achieved by features in the analyzer that purge the sensor, including the sensing element and all passages, cavities, and components in the vicinity of the sensing element, such as for example the desiccant, with zero air, defined herein as air that is substantially free of $NO_x$. Preferably, the purging air is substantially free of all species that bind to the protein in a way that interferes with the ability of the sensing element to detect and quantify nitric oxide. Such features can include a gas pump, a filter, particular one that removes $NO_x$, one or more valves that select among various inputs to the pump, and a timer to set the position of the valve(s) and the time intervals between changes in the valve position(s). These features can operate in conjunction with a carbon dioxide filter, a diffusion barrier to limit the rate of, or prevent, diffusion of atmospheric air into the analyzer through the analyzer vent opening, and the analyzer optical system that exposes the sensor to light for absorption measurements, at least some, and preferably all, of which are present in preferred embodiments of the analyzer. In preferred embodiments as well, the timer is programmable to set and adjust the time intervals for the different valve positions, to perform the purging in pulses during each regeneration cycle and to select the number of pulses, to allow the system to stabilize prior to taking measurements, to coordinate the actuation of the sensor light source with the purging function to minimize any effect that exposure to the light source may have on the encapsulated protein, and generally to control the timing and direction of all gas flows into and/or through the analyzer. Thermal equilibration is also present in preferred embodiments, and the timer in these embodiments will also set a period of time at the end of each purging cycle to allow the sensor to recover.

These and other features, objects, and advantages of the invention will be apparent from the description that follows.

BRIEF DESCRIPTION OF THE DRAWING

The FIGURE attached hereto is a schematic representation of a nitric oxide analyzer in accordance with the present invention.

DETAILED DESCRIPTION OF THE INVENTION AND PREFERRED EMBODIMENTS

The $NO_x$-free air, also known as "zero air," that is used for the purge of the sensor, including the nitric oxide-binding protein and the components associated with the protein, is preferably obtained in accordance with this invention by drawing atmospheric air through a $NO_x$ filter in the analyzer. The expression "$NO_x$-free air" is used herein to denote air that contains substantially zero parts per billion (ppb) of oxides of nitrogen, and the expressions "substantially zero" and "substantially free" denote either a total absence of the species in question or an amount lower than the lower limit of detection of the detector in the system. In most cases, an error margin of up to 3 ppb will acceptably meet the definition of "substantially zero ppb," although an error margin of up to 1 ppb is preferred. The expression "NO." is used here as it is in the art, which is to denote any of various oxides of nitrogen that are common components of atmospheric air, most commonly nitric oxide (NO) and nitrogen dioxide ($NO_2$).

A common example of an $NO_x$ filter is a packed bed of solid granules of an NO adsorbent, such as any of the adsorbents known in the art for this purpose. Examples of such adsorbents are alumina, calcium carbonate, calcium oxide, calcium sulfate, barium oxide, sodium carbonate, sodium phosphate, potassium carbonate, potassium permanganate, and molecular sieves such as molecular sieve 13X. Potassium permanganate is preferred. The packed bed is conveniently and commonly supplied in cartridge form, and an example of a supplier of such cartridges is City Technology Limited, Des Plaines, Ill. USA.

In embodiments of the invention in which the regeneration cycle includes thermal equilibration of the sensor, a heating or cooling device is included in the analyzer and set to a temperature at which the sensor will function at optimal sensitivity and one that will provide the most consistent and reproducible results in nitric oxide detection. One example of such a device is a thermoelectric ("Peltier") device, of which the design and operation are well known in the field of laboratory apparatus. Thermoelectric devices are widely available from commercial suppliers of components for laboratories and laboratory equipment manufacturers. Preferred temperatures are those within the range of about 25° C. to about 35° C., more preferably about 27.5° C. to about 32.5° C., and most preferably about 30° C.±0.5° C. Thermal equilibration at the completion of purging is preferably performed for a period of about one minute to about fifteen minutes.

The purging protocol can assume a variety of forms, examples of which are continuous purging, variable purging in a waveform of purge rate vs. time, and pulsed purging. The protocol will be selected to achieve full reconditioning of the sensor in a minimum period of time and yet to minimize the exposure of the sensor to ambient air. Particularly preferred protocols are those in which purging is performed in pulses, separated by static intervals with no gas movement through the sensor, i.e., while the atmosphere surrounding the sensor is static. The duration and number of pulses, as well as the durations of the static intervals, can vary. In most cases, best results will be obtained with pulses lasting from about one second to about ten seconds each, and static intervals lasting from about ten seconds to about three minutes each. In preferred operations, the pulses last from about two seconds to about six seconds each, and the static intervals last from about thirty seconds to about two minutes each. In a presently preferred embodiment, each pulse is four seconds in duration and the static intervals are such that the pulses occur once a minute. A presently preferred protocol with this timing sequence is a single pulse following a breath sample in which the nitric oxide concentration was 59 ppb or less, two pulses when the nitric oxide concentration was within the range of 60 ppb to 99 ppb, four pulses when the nitric oxide concentration was within the range of 100 ppb to 149 ppb, and five pulses when the nitric oxide concentration was 150 ppb or greater. The monitor can be programmed to determine the minimum number of pulses needed following a given sample. Thermal equilibration of the sensor can be performed either independently of or concurrently with the purging of the sensor. Since in most cases a thermoelectric device controlling the sensor temperature will be activated at all times, thermal equilibration continues during both the pulses and the static intervals between the pulses.

The sensor will contain as its active component a protein that binds nitric oxide and undergoes an optically detectable change when nitric oxide binding has occurred. The change can be detected visually or by instrumentation, and can be a change in absorption, reflection, light scattering, emission following excitation, or any such change known in the art, and can be either visually observed, displayed on a monitor, or recorded electronically, and it can also be analyzed an quantified. Detection is preferably performed by optical absorbance spectroscopy. A variety of nitric oxide-binding proteins can be used, and a preferred example is cytochrome C. The protein is encapsulated in a matrix of an inert but porous material, the porosity being sufficient to allow gaseous nitric oxide to diffuse into the interior of the matrix to contact the protein. Preferred matrices are sol-gels, of which aerogels and xerogels are preferred. The protein and matrix combination, in its preferred form, is referred to herein as a "monolith" to denote its solid form and continuous, unitary composition. The optimum protein concentration of the protein in the monolith is a function of the pore size of the matrix, the tortuosity of the matrix, the molecular size of the protein, and the colligative properties of the protein during the formation of the monolith. When cytochrome C is used, a preferred protein concentration in the xerogel in certain embodiments of this invention is from about 20 mg/cc to about 27 mg/cc. In other embodiments, the preferred cytochrome C concentration is from about 8 mg/cc to about 15 mg/cc, most preferably from about 12 mg/cc to about 15 mg/cc, with a value of approximately 14 mg/cc particularly preferred.

The sensing element can be in the form of a thin film, for example one with a thickness of from about 250 nm to about 1,000 nm with a cytochrome c concentration of about 10 mg/cc to about 20 mg/cc prior to shrinkage of the matrix. Shrinkage commonly occurs during curing and drying of the matrix, and results in an approximately doubling of the cytochrome C concentration. Alternatively, the sensing element can be a monolith, likewise subject to the same shrinkage. In either case, the sensing element preferably has a peak optical density of about 2.8 absorbance units at 400 nm. Preferred sensing elements are those that detect nitric oxide in exhaled breath at levels of 300 ppb or less, and in many cases 200 ppb or less. Within its limits of detection, the sensing element can indicate an absence of NO, or in some cases a lower limit of 5 ppb or 10 ppb. A monolith sensing element that is prepared from a solution containing 0.092 mM or 1.1 mg/cc of cytochrome C will respond quickly, i.e., in less than one minute, to nitric oxide at concentrations below 50 ppb. When the solution concentration of cytochrome C is raised to 0.46 mM or 5.7 mg/cc, the response rate decreases to about one-tenth of its value at the lower concentration. The preferred monolith has a pore network with a pore width of from 3.0 nm to 6.0 nm, preferably from 3.5 nm to 5.8 nm, and a surface area of about 550 to about 650 $m^2$/g. Upon shrinkage of the monolith during curing and drying, the cytochrome C concentration rises from 0.092 mM solution to $(2.2)^3 \times 0.092 = 0.98$ mM or $(2.2)^3 \times 1.1 = 11.71$ mg/cc. These concentrations approach, but do not equal, the maximum concentration of cytochrome C allowable for a fast-responding monolith. With this in mind, the maximum allowable concentrations of cytochrome C in fast-responding thin films and monoliths for trace gas sensors are both close to 2 mM or approximately 25 mg/cc in the final xerogel state. The term "trace gas" is used herein to denote a gas at a concentration in the ppb range, preferably, as noted above, 200 ppb or less.

The sensor preferably includes, in addition to the encapsulated protein, a desiccant that controls both the moisture level and the nitric oxide level of the regions of the sensor and the analyzer itself in the vicinity of the encapsulated protein, without affecting the ability of the sensor to differentiate between different nitric oxide levels in the exhaled breath samples. A preferred desiccant is one that will absorb nitric oxide but only at a slow rate relative to the rate at which the sample flows through the sensor. The desiccant thus moderates abrupt changes in the nitric oxide concentration in the adjacent regions, while limiting any variations in the water concentration during the testing period to less than 1 ppm. Molecular sieves are effective desiccants, particularly molecular sieve 3A. The desiccant will also maintain the monolith at a moisture level of approximately 10 ppm to 2,000 ppm.

The sensor is contained in a measurement cell, which also includes a light source, a port for the passage of light through the matrix, a reference port for the passage of light from the same light source, and two absorbance detectors, one associated with each of the two ports. The light source can be a light-emitting diode (LED), a laser, an incandescent light source, or a fluorescent light source, and can be one that produces either broad spectrum light or light of a narrow band of wavelengths. The preferred light source is an LED emitting light within the wavelength range of 395 nm to 460 nm. The absorbance detectors can be photodiodes or any comparable devices. In preferred embodiments of the invention, the light source is turned off during the entire regeneration cycle and whenever the system is not in use, since nitric oxide-binding proteins suitable for use in the sensor are generally susceptible to decomposition, denaturation, or otherwise inactivation during prolonged exposure to light. In further preferred embodiments, the monitor contains a memory component that monitors the total amount of light energy to which the sensor is exposed, as a further means of prolonging the useful life of the sensor.

The diffusion barrier that limits the rate of back diffusion of atmospheric air into the analyzer, or prevents such back diffusion entirely, can be a valve, such as a check valve, or an elongated conduit of small cross section, the length and cross section of which serve as the means of reducing the diffusion rate. While the actual dimensions are not critical and can vary with the capacity of the instrument and the construction of the other parts of the instrument, a conduit that will serve this purpose in most cases is one with a length greater than 10 cm and an inner diameter of less than 0.25 cm$^2$. In a presently preferred example, the length is approximately 50 cm and the inner diameter is approximately 0.15 cm$^2$. Other diffusion barriers will be readily apparent to those skilled in the art.

Preferred analyzers of the present invention contain a pump or other gas conveyance component to control the rate at which exhaled breath and purge gas flow through the analyzer passages. The term "pump means" is used generically herein to denote any device that will impose movement on the gas and also modulate the gas flow rate to maintain it within a range that will allow the analyzer to function most effectively. Conventional gas pumps can be used, including fans, blowers, and compressors, both of the positive displacement and rotary types.

The FIGURE hereto depicts a component diagram of one example of an analyzer 10 in accordance with the present invention. The user exhales directly into a breath intake port 11 which leads to a breath inlet line 12, and the pressure of the exhaled breath is measured by the analyzer and shown on a monitor included on the analyzer. The flow of the user's breath in the inlet line 12 is also controlled by a breath pump 13. Branching off of the breath inlet line 12 is a sampling line 15 equipped with a switching valve 16 that switches on command between two inlets to flow through a common outlet. The term "switching valve" is used herein to denote any device that can be switched in this manner, including those operated by solenoid, those operated by pneumatic means, and all conventional geometries for such valves. The inlets in this case are the sampling line 15 and a line for NO$_x$-free air 17, and the outlet is a line 18 leading to a sample filter 19 (i.e., a filter to remove carbon dioxide), a sample pump 20, the measurement cell 21 containing the sensor 22 surrounded by the desiccant 23, and finally through a discharge line 24 and out to vent. The line 17 for NO$_x$-free air contains an online NO$_x$ filter 25 and is open to ambient air, optionally with a valve to isolate the system from ambient air during an analysis cycle. Further components of the analyzer are a controller 31 containing a timer 32 and a display 33, the controller governing the two pumps 13, 20 and the switching valve 16.

An example of a procedure for multiple uses of the analyzer without removing the sensor after each use is as follows.

(1) With a fresh sample filter 19 and a fresh sensor 22 inserted in the analyzer and the switching valve 16 in a position communicating the NO$_x$ filter 25 with line 18 leading to the sample filter 19, the sample pump 20 is energized and allowed to run for four seconds. With the switching valve 16 in this position, the sample filter 19, sensor 22, and any dead volume in the sample section of the analyzer are purged of atmospheric nitric oxide that may have entered the analyzer from the environment.

(2) The sample pump 20 is then turned off and the sensor is allowed to recover. Recovery is performed for 4.5 minutes with no gas flow through the analyzer.

(3) The light source in the measurement cell is then turned on, and baseline absorbance is detected by a photodiode and monitored by the analyzer for at least thirty seconds. Once the analyzer determines that the signal has stabilized, the monitor displays a message that the analyzer is ready for a breath test.

(4) Upon the appearance of this message, the patient exhales into the breath intake port 11 while watching the monitor to achieve a substantially steady breath rate, and the breath pump 13 is actuated to achieve a breath flow rate of three liters per minute. With the position of the switching valve 16 as yet unchanged, all of the breath that has been received in the analyzer is drawn through the breath pump 13 and discharged through the breath outlet port 14. This condition is continued for 6.5 seconds to purge gas from any dead volume in the analyzer that has not already been purged of NO$_x$ through the sample pump 20 in step (1) above, and to discard an initial portion of the gas from the patient's lungs.

(5) The switching valve 16 is then switched to its second position, in which the breath inlet line 12 is placed in communication with line 18 leading to the sample filter 19, sample pump 20, and measurement cell 21, and the sample pump 20 is turned on, causing a sample of breath to pass through the sensor 22. This is continued for four seconds, after which the sample pump 20 is turned off and the breath sample is isolated in the measurement cell in contact with the sensor. The latter condition is maintained for forty-six seconds, during which the absorbance of the light by the cytochrome C in the sensor is measured, and the analytical result is calculated by the analyzer and displayed on the monitor. At this point the analysis is complete.

(6) Once the analysis is complete, the light source is turned off, and the switching valve 16 is returned to its original position communicating the NO$_x$ filter 24 with the line 18 leading to the sample filter 19, sample pump 20, and measurement cell 21. The analyzer is now ready for regeneration.

(7) To regenerate the analyzer, the sample pump 20 is turned on to draw atmospheric air through the NO$_x$ filter and through the measurement cell. This flow of NO$_x$-free air through the measurement cell is continued for four seconds and results in the removal of nitric oxide from the regions surrounding the monolith and the desiccant where nitric oxide has accumulated from the breath sample. This four-second pulse is followed by a static interval with the sample pump turned off while the thermoelectric device, which is operating at all times, remains on to allow the sensor to recover. When two or more pulses are performed, the pulses thus occur at one-minute intervals. After the last pulse, the analyzer is given a recovery period of 4.5 minutes before a new test is performed. To perform the analysis on a new sample, steps (3) through (6) are then followed. If more than four hours has passed after regeneration, the procedure is begun at step (1) with a single purge prior to a breath test. Regeneration in accordance with this invention renders the analyzer effective in producing accurate measurements of nitric oxide in exhaled breath at levels well below 60 ppb and higher.

The timer 32 that turns the pumps 13, 20 on and off and controls the position of the switching valve 16 can be any conventional component. An on-board microprocessor of any of the types well known in the art can be used.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A method for treating an analyzer for detecting gaseous nitric oxide levels in human exhalation so that said analyzer will produce reproducible results upon analyzing a succession of samples of exhaled breath, said method comprising:
    purging a nitric oxide sensor of the analyzer with filtered atmospheric air that is substantially $NO_x$-free between analyses, the purging including:
    drawing atmospheric air through a $NO_x$-filter of the analyzer to filter the atmospheric air of $NO_x$ and establish a purge gas; and
    passing the purge gas through a measurement cell containing the sensor;
    wherein the sensor includes:
    (i) a protein that binds nitric oxide contained in exhaled breath and that undergoes an optically detectable change upon so binding, said protein immobilized in a porous inert matrix at a protein concentration that together with said matrix porosity causes exhaled breath containing 200 ppb or less of nitric oxide to produce said optically detectable change, and
    (ii) a desiccant that maintains a controlled moisture level in said matrix without affecting the ability of the analyzer to differentiate between samples containing different nitric oxide levels.

2. The method of claim 1 comprising purging said nitric oxide sensor between analyses with air that is substantially free of all species that bind to said protein.

3. The method of claim 1 wherein said optically detectable change is a change in light absorbance, said analyzer further comprises a light source directed at said sensor and an absorbance detector to measure changes in absorbance in said sensor, and said method further comprises keeping said light source inactivated during said purging and when the analyzer is not in use.

4. The method of claim 1 wherein said purging consists of a succession of pulses of said substantially $NO_x$-free air separated by static intervals with substantially no gas flow through said sensor.

5. The method of claim 4 wherein said purging comprises from two said pulses to ten said pulses, each pulse ranging in duration from about one second to about ten seconds, and said static intervals ranging in duration from about ten seconds to about 3 minutes.

6. The method of claim 4 wherein said purging comprises from two said pulses to five said pulses, each pulse ranging in duration from about two seconds to about six seconds, and said static intervals ranging in duration from about thirty seconds to about two minutes.

7. The method of claim 1 further comprising thermally equilibrating said sensor to a temperature of from about 25° C. to about 35° C. subsequent to said purging.

8. The method of claim 7 wherein said thermal equilibration is performed for duration of from about one minute to about fifteen minutes.

9. The method of claim 1 wherein said analyzer further comprises a $CO_2$ filter, and said method further comprises passing said substantially $NO_x$-free air through said $CO_2$ filter before purging said nitric oxide sensor with said substantially $NO_x$-free air.

10. The method of claim 1 wherein said $NO_x$ filter comprises a packed bed of potassium permanganate or a molecular sieve 13x.

11. The method of claim 1 wherein said protein is cytochrome C.

12. The method of claim 1 wherein said protein is cytochrome C and said matrix is a xerogel.

13. The method of claim 1 wherein said desiccant is molecular sieve 3A.

14. The method of claim 1 wherein said protein is cytochrome C, said matrix is a xerogel or an aerogel, and said cytochrome C and matrix together form a monolith with a concentration of from about 1 mg to about 40 mg cytochrome C per cubic centimeter of said monolith, a monolith pore diameter of from about 2 nm to about 10 nm, and a monolith surface area of from about 550 $m^2/g$ to about 650 $m^2/g$.

* * * * *